United States Patent [19]
Cooke et al.

[11] Patent Number: 5,945,452
[45] Date of Patent: *Aug. 31, 1999

[54] TREATMENT OF VASCULAR DEGENERATIVE DISEASES BY MODULATION OF ENDOGENOUS NITRIC OXIDE PRODUCTION OR ACTIVITY

[75] Inventors: John P. Cooke, Palo Alto; Victor J. Dzau, Los Altos; Gary H. Gibbons, Palo Alto, all of Calif.

[73] Assignee: The Board of Trustees of the Leland Stanford Junior University

[ * ] Notice: This patent is subject to a terminal disclaimer.

[21] Appl. No.: 08/796,298

[22] Filed: Feb. 7, 1997

Related U.S. Application Data

[63] Continuation of application No. 08/336,159, Nov. 8, 1994, abandoned, which is a continuation-in-part of application No. 08/076,312, Jun. 11, 1993, Pat. No. 5,428,070.

[51] Int. Cl.$^6$ .............................. A23L 1/305; A61K 9/00; A61K 31/195
[52] U.S. Cl. ...................... 514/564; 424/439; 424/441; 426/648; 426/656; 514/565
[58] Field of Search ........................ 930/290; 530/358; 426/648, 656, 657; 514/310, 557, 564, 565, 20; 424/439, 441

[56] References Cited

U.S. PATENT DOCUMENTS

| | | | |
|---|---|---|---|
| 4,154,813 | 5/1979 | Kleinberg | 530/330 |
| 4,920,098 | 4/1990 | Cotter et al. | 514/2 |
| 4,954,526 | 9/1990 | Keefer | 514/149 |
| 5,032,608 | 7/1991 | Dudrick | 514/423 |
| 5,106,836 | 4/1992 | Clemens et al. | 514/21 |
| 5,157,022 | 10/1992 | Barbul | 514/18 |
| 5,217,997 | 6/1993 | Levere et al. | 514/565 |
| 5,278,189 | 1/1994 | Rath et al. | 514/561 |
| 5,385,937 | 1/1995 | Stamler et al. | 514/557 |
| 5,411,956 | 5/1995 | Miyazaki et al. | 514/15 |
| 5,428,070 | 6/1995 | Cooke et al. | 514/557 |
| 5,543,430 | 8/1996 | Kaesemeyer et al. | 514/565 |
| 5,767,160 | 6/1998 | Kaesemeyer et al. | 514/565 |
| 5,780,039 | 7/1998 | Greenberg et al. | 424/400 |

FOREIGN PATENT DOCUMENTS

| | | |
|---|---|---|
| 546796 | 6/1993 | European Pat. Off. . |

OTHER PUBLICATIONS

Rocic et al. L-arginyl-L-lysine and L-arginyl-L-arginine in Med. Sci. Res. 1990, vol. 18, pp. 165–166.

McNamara et al. L-Arginine Inhibits Ballon Catheter-Induced . . . Biochem. Biophys.Res. Comm. May 28, 1993, vol. 193, No. 1, pp. 291–296.

*Primary Examiner*—Jeffrey E. Russel
*Attorney, Agent, or Firm*—Bertram I. Rowland; Flehr Hohbach Test Albritton & Herbert LLP

[57] ABSTRACT

Atherogenesis and restenosis are treated by long term administration of physiologically acceptable compounds which enhance the level of endogenous nitric oxide or other intermediates in the NO induced relaxation pathway in the host. Alternatively, or in combination, other compounds may be administered which provide for short term enhancement of nitric oxide, either directly or by physiological processes. In addition, cells may be genetically engineered to provide a component in the synthetic pathway to nitric oxide, so as to drive the process to enhance nitric oxide concentration, particularly in conjunction with the administration of a nitric oxide precursor.

10 Claims, 9 Drawing Sheets

TREATMENT OF VASCULAR DEGENERATIVE DISEASES BY MODULATION OF ENDOGENOUS NITRIC OXIDE PRODUCTION OR ACTIVITY

CROSS-REFERENCE TO RELATED APPLICATIONS

This application is a continuation of application Ser. No. 08/336,159, filed Nov. 8, 1994, now abandoned, which is a continuation-in-part application of Ser. No. 08/076,312 filed Jun. 11, 1993 now U.S. Pat. No. 5,428,070.

INTRODUCTION

This invention was supported in part by the United States Government under Grant 1KO7HCO2660 (NHLBI). The U.S. Government may have an interest in this application.

TECHNICAL FIELD

The field of this invention is the modulation of NO activity, which finds application in the treatment of vascular degenerative diseases, particularly atherosclerosis, thrombosis and restenosis.

BACKGROUND

Atherosclerosis and vascular thrombosis are a major cause of morbidity and mortality, leading to coronary artery disease, myocardial infarction, and stroke. Atherosclerosis begins with an alteration in the endothelium, which lines the blood vessels. The endothelial alteration results in adherence of monocytes, which penetrate the endothelial lining and take up residence in the subintimal space between the endothelium and the vascular smooth muscle of the blood vessels. The monocytes absorb increasing amounts of cholesterol (largely in the form of oxidized or modified low-density lipoprotein) to form foam cells. Oxidized low-density lipoprotein (LDL) cholesterol alters the endothelium, and the underlying foam cells distort and eventually may even rupture through the endothelium.

Platelets adhere to the area of endothelial disruption and release a number of growth factors, including platelet derived growth factor (PDGF). PDGF, which is also released by foam cells and altered endothelial cells, stimulates migration and proliferation of vascular smooth muscle cells into the lesion. These smooth muscle cells release extracellular matrix (collagen and elastin) and the lesion continues to expand. Macrophages in the lesion elaborate proteases, and the resulting cell damage creates a necrotic core filled with cellular debris and lipid. The lesion is then referred to as a "complex lesion." Rupture of this lesion can lead to thrombosis and occlusion of the blood vessel. In the case of a coronary artery, rupture of a complex lesion may precipitate a myocardial infarction, whereas in the case of a carotid artery, stroke may ensue.

One of the treatments that cardiologists and other interventionalists employ to reopen a blood vessel which is narrowed by plaque is balloon angioplasty (approximately 300,000 coronary and 100,000 peripheral angioplasties are performed annually). Although balloon angioplasty is successful in a high percentage of the cases in opening the vessel, it unfortunately denudes the endothelium and injures the vessel in the process. This damage causes the migration and proliferation of vascular smooth muscle cells of the blood vessel into the area of injury to form a lesion, known as myointimal hyperplasia or restenosis. This new lesion leads to a recurrence of symptoms within three to six months after the angioplasty in a significant proportion of patients (30–40%).

Because of their great prevalence and serious consequences, it is critically important to find therapies which can diminish the incidence of atherosclerosis, vascular thrombosis and restenosis. Ideally, such therapies would inhibit the pathological processes associated with atherosclerosis, thereby providing prophylaxis or retarding the progression of the degenerative process.

As briefly summarized above, these pathological processes are extremely complex, involving a variety of different cells which undergo changes in their character, composition, and activity, as well as in the nature of the factors which they secrete and the receptors that are up- or down-regulated. A substance released by the endothelium, "endothelium derived relaxing factor" (EDRF), may play an important role in inhibiting these pathologic processes. EDRF is now known to be nitric oxide (NO) or a labile nitroso compound which liberates NO. (For purposes of the subject invention, unless otherwise indicated, nitric oxide (NO) shall intend nitric oxide or the labile nitroso compound which liberates NO.) This substance has been reported to relax vascular smooth muscle, inhibit platelet aggregation, inhibit mitogenesis and proliferation of cultured vascular smooth muscle, and leukocyte adherence. NO may have other effects, either direct or indirect, on the various cells associated with vascular walls and degenerative diseases of the vessel.

Relevant Literature

Girerd, et al. (1990) Circulation Research 67, 1301–1308 report that intravenous administration of L-arginine potentiates endothelium-dependent relaxation in the hind limb of cholesterol-fed rabbits. The authors conclude that synthesis of EDRF can be increased by L-arginine in hypercholesterolemia. Rossitch, et al. (1991) J. Clin. Invst. 87, 1295–1299 report that in vitro administration of L-arginine to basilar arteries of hypercholesterolemic rabbits reverses the impairment of endothelium-dependent vasodilation and reduces vasoconstriction. They conclude that the abnormal vascular responses in hypercholesterolemic animals is due to a reversible reduction in intracellular arginine availability for metabolism to nitric oxide.

Creager, et al. (1992) J. Clin. Invest. 90, 1248–1253, report that intravenous administration of L-arginine improves endothelium-derived NO-dependent vasodilation in hypercholesterolemic patients.

Cooke, et al., "Endothelial Dysfunction in Hypercholesterolemia is Corrected by L-arginine," Endothelial Mechanisms of Vasomotor Control, eds. Drexler, Zeiher, Bassenge, and Just; Steinkopff Verlag Darmstadt, 1991, pp. 173–181, review the results of the earlier references and suggest, "If the result of these investigations may be extrapolated, exogenous administration of L-arginine (i.e., in the form of dietary supplements) might represent a therapeutic adjunct in the treatment and/or prevention of atherosclerosis."

Cooke, (1990) current Opinion in Cardiology 5, 637–644 discusses the role of the endothelium in the atherosclerosis and restenosis, and the effect that these disorders have on endothelial function.

Cooke (1992) J. Clin. Invest. 90, 1168–1172, describe the effect of chronic administration of oral L-arginine in hypercholesterolemic animals on atherosclerosis. This is the first demonstration that oral L-arginine supplements can improve the release of NO from the vessel wall. The increase in NO release from the vessel wall was associated with a striking reduction in atherosclerosis in hypercholesterolemic animals. This is the first evidence to support the hypothesis that increasing NO production by the vessel wall inhibits the development of atherosclerosis.

Cooke and Tsao, (1992) Current Opinion in Cardiology 7, 799–804 describe the mechanism of the progression of atherosclerosis and suggest that inhibition of nitric oxide may disturb vascular homeostasis and contribute to atherogenesis.

Cooke and Santosa, (1993) In: Steroid Hormones and Dysfunctional Bleeding, AAAS Press, review the activities of EDRF in a variety of roles and suggest that reversibility of endothelial dysfunction may be affected by the stage of atherosclerosis. They conclude that EDRF is a potent vasodilator, plays a key role in modulating conduit and resistance vessel tone, has important effects on cell growth and interactions of circulatory blood cells with a vessel wall, and that disturbances of EDRF activity may initiate or contribute to septic shock, hypertension, vasospasm, toxemia and atherosclerosis.

Fitzpatrick, et al., American Journal of Physiology 265 (Heart Circ. Physiol. 34):H774–H778, 1993 report that wine and other grape products may have endothelium-dependent vasorelaxing activity in vitro.

Wang et al., J. Am. Cell. Cardiol. 23:452–458, 1994, report that oral adminstration of arginine prevents atherosclerosis in the coronary arteries of hypercholesterolemic rabbits.

Noruse et al., Arterioscler. Thromb. 14:746–752, 1994, report that oral administration of an antagonist of NO productioin accelerates atherogenesis in hypercholesterolemic rabbits.

Cayette et al., Arterioscler. Thromb. 14:753–759, 1994 alsoreport that oral administration of an antagonnist of NO production accelerates plaque development in hypercholesterolemic rabbits.

Other references which refer to activities attributed to NO or its precursor include: Pohl and Busse (1989) Circ. Res. 65:1798–1803; Radomski et al. (1987) Br. J. Pharmacol. 92:181–187; and Stamler et al. (1989) Circ. Res. 65:789–795; anti-platelet activity); Garg and Hassid (1989) J. Clin. Invest. 83:1774–1777; and Weidinger et al, (1990) Circulation 81:1667–1679; NO activity in relation to vascular smooth muscle growth); Ross (1986) N. Engl. J. Med. 314:488–500; Bath et al. (1991) Arterioscler. Thromb. 11:254–260; Kubes et al. (1991) Proc. Natl. Acad. Sci. USA 89:6348–6352; Lefer et al. (1990) In: Endothelium-Derived Contracting Factors. Basel, S. Karger, pp. 190–197; NO activity in relation to leukocyte adhesion and migration); Heistad et al. (1984) Circ. Res. 43:711–718; Rossitch et al. (1991) J. Clin. Invest. 87:1295–1299; Yamamoto et al. (1988) ibid 81:1752–1758; Andrews et al. (1987) Nature 327:237–239; Tomita et al. (1990) Circ. Res. 66:18–27; Kugiyama et al. (1990) Nature 344:160–162; Mitchell et al. (1992) J. Vasc. Res. 29:169 (abst.); and Minor et al. (1990) J. Clin. Invest. 86:2109–2116; NO activity in relation to hypercholesterolemia); Tanner et al. (1991) Circulation 83:2012–2020; Kuo et al. (1992) Circ. Res. 70:f465–476; Drexler et al. (1991) Lancet 338:1546–1550; and Nakanishi et al. (1992) In: Scientific Conference on Functional and Structural Mechanisms of Vascular Control, Snowbird, UT, p. 86 (abstr.); relation of L-arginine to NO-dependent vasodilation.

SUMMARY OF THE INVENTION

Methods are provided for modulating cellular adhesion, infiltration and proliferation by modulating the level of nitric oxide or active precursor at a physiological site. The methods find use in the treatment of atherosclerosis, restenosis and thrombosis. The enhancement of endogenous nitric oxide or secondary messenger availability at a physiological site inhibits the progression of atherosclerosis, restenosis and thrombosis. As a prophylaxis or treatment for atherosclerotic susceptible hosts, the agent is chronically administered at an effective dosage. For restenosis, the agent may be administered for a limited period since this pathological process generally abates 3–6 months after the vascular injury (i.e. angioplasty or atherectomy). Oral administration of L-arginine, precursors to L-arginine, e.g. oligopeptides or polypeptides comprising L-arginine, or proteins comprising high levels of L-arginine, by itself or in combination with L-lysine, as a dietary supplement will increase NO elaboration and thereby diminish the effects of atherogenesis. Other techniques to enhance NO or secondary messenger availability may be utilized such as increasing the availability of NO synthase, for example, as a result of enhanced expression of NO synthase in the vessel wall, particularly at the lesion site, release of NO from the vessel wall or reduction of degradation of NO or the secondary messenger, cyclic guanosine monophosphate ("cGMP").

DESCRIPTION OF SPECIFIC EMBODIMENTS

Figure 1:
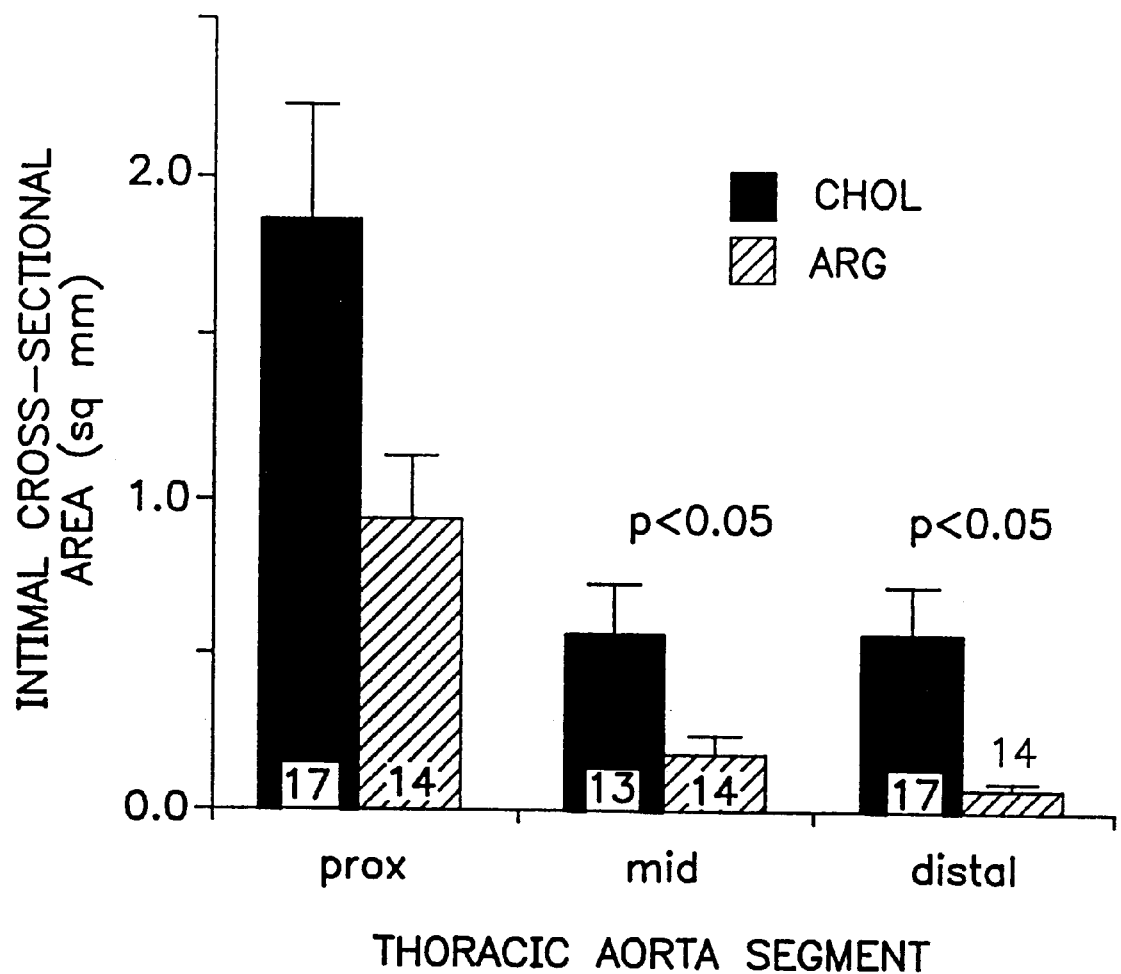
FIG. 1 is a bar diagram of histomorphometric studies of the effect of L-arginine on atherosclerotic plaque in hypercholesterolemic animals (See Ex. 1)

In accordance with the subject invention, common vascular degenerative diseases such as atherosclerosis, restenosis, and vascular thrombosis, are treated prophylactically and/or therapeutically by enhancing the level or activity of endogenous nitric oxide. The enhanced level or activity of nitric oxide (which is intended to include any precursor of nitric oxide which results in such enhanced level) can be achieved by modulating the activity, synthesis or concentration of any of the components associated with the formation of nitric oxide in the nitric oxide synthetic pathway, or inhibiting the rate of degradation of nitric oxide, its precursors, or the secondary messengers associated with the relaxation signal. In referring to the enhanced level or activity, the term "effect" will be used to encompass the two situations. The enhanced effect of nitric oxide may be a result of oral or intravenous administration to the patient of a precursor in the metabolic pathway to the production of nitric oxide (such as L-arginine, L-lysine, polypeptides comprising these amino acids, and the like), providing an enzyme in the metabolic pathway to NO, particularly NO synthase, by introduction of the gene for NO synthase under conditions for integration of the gene into the endothelial or other cells and expression of the gene, or by directly adding an enzyme associated with the production of nitric oxide. The enhanced level of nitric oxide may also result from administration of an agent to protect the NO from degradation, such as an oxidant or su peroxide dismutase. The agent will be administered in a form of other than a natural food source, such as meat or plants as natural protein sources, fruits or products derived therefrom, e.g. wine, or the like.

One approach is to employ L-arginine and/or L-lysine, as individual amino acids, in combination, or as a precursor to L-arginine, e. g. a monomer of a polypeptide, as a dietary supplement. The amino acid(s) are administered as any physiologically acceptable salt, such as the hydrochloride salt, glutamate salt, etc. They can also be administered as a peptide (i.e. poly-L-arginine) so as to increase plasma levels of the NO precursor. Oligopeptides of particular interest include oligopeptides of from 2 to 30, usually 2 to 20, preferably 2 to 10 amino acids, having at least 50 mol % of L-arginine, preferably at least about 75 mol % of L-arginine and L-lysine, more preferably having at least about 75 mol % of L-arginine. The oligopeptides can be modified by being ligated to other compounds, which can enhance absorption from the gut, provide for enhancement of NO synthesis or stability, e.g. reducing agents and antioxidants, and the like.

Naturally occurring sources include protamine or other naturally occurring L-arginine or -lysine containing protein, which is high in one or both of the indicated amino acids, e.g. greater than about 40%, preferably greater than about 50%.

The administration of L-arginine or other convenient NO precursor would be in accordance with a predetermined regimen, which would be at least once weekly and over an extended period of time, generally at least one month, more usually at least three months, and as a chronic treatment, could last for one year or more, including the life of the host. The dosage administered will depend upon the frequency of the administration, the blood level desired, other concurrent therapeutic treatments, the severity of the condition, whether the treatment is for prophylaxis or therapy, the age of the patient, the natural level of NO in the patient, and the like. Desirably, the amount of L-arginine or biologically equivalent compound which is used would generally provide a plasma level in the range of about 0.2 mM to 30 mM. The oral administration of L-arginine can be achieved by providing L-arginine or other No precursor as a pill, powder, capsule, liquid solution or dispersion, particularly aqueous, or the like. Various carriers and excipients may find use in formulating the NO precursor, such as lactose, terra alba, sucrose, gelatin, aqueous media, physiologically acceptable oils, e.g. peanut oil, and the like. Usually, if daily, the administration of L-arginine and/or L-lysine for a human host will be about 1 to 12 g per day.

Furthermore, other agents can be added to the oral formulation of the amino acids or polypeptides to enhance their absorption, e.g. pyridoxal phosphate, which is known to enhance amino acid absorption. The amount of pyridoxal phosphate would be the conventional amount used with amino acids for such purpose. Furthermore, agents known to protect NO from degradation, such as antioxidants (e.g. Vitamin C, Vitamin E, β-carotene or probucol) or superoxide dismutase, can be added to the oral or intravenous formulations of arginine or arginine-containing peptides. Formulations of particular interest include other amino acids, particularly L-lysine, to enhance the action or absorption of L-arginine, usually in a mol amount in relation to L-arginine of from about 0.1 to 1 to 1.

The administration of L-arginine can be administered prophylactically, so as to inhibit atherogenesis or restenosis, or therapeutically after atherogenesis has been initiated. Thus, for example, a patient who is to undergo balloon angioplasty can have a regimen of L-arginine administered substantially prior to the balloon angioplasty, preferably at least about a week or substantially longer. Alternatively, in a patient where atherogenesis is suspected, the administration of L-arginine can begin at any time. Of particular interest is the incorporation of L-arginine as a supplement in a food, such as a health bar, e.g. granola, other grains, fruit bars, such as a date bar, fig bar, apricot bar, or the like. The amount of L-arginine or the equivalent would be about 2–25 g per dosage or bar, preferably about 3–15 g.

Instead of oral administration, intravascular administration can also be employed, particularly where more rapid enhancement of the nitric oxide level in the vascular system is desired (i.e. as with acute thrombosis of a critical vessel), so that combinations of oral and parenteral administrations can be employed in accordance with the needs of the patient. Furthermore, parenteral administration can allow for the administration of compounds which would not readily be transported across the mucosa from the gastrointestinal tract into the vascular system.

Another approach is to administer the active ingredient of grape skin extract, which is known to enhance NO activity. See Fitzpatrick et al. (1993), supra. The extract can be enriched for the active componenent by employing separation techniques and assaying the activity of each of the fractions obtained. The grape skin extract can be divided into fractions using in a first gel permeation separation to divide the extract by the size of the components. The active fraction(s) can be determined by an appropriate assay, see the experimental section. The active fraction(s) can be further separated using HPLC and an appropriate eluent, conveniently either an isocratic eluent of aqueous acetonitrile or propanol or a linearly varying eluent, using the same solvents. Fractions which are shown to be active and substantially pure, e.g. at least 80 weight %, by thin layer chromatography, mass spectrometry, gas phase chromatography, or the like can then be characterized using infra-red, nuclear magnetic resonance, mass or other spectroscopy.

For oral or intravascular administration, one can provide L-arginine, by itself or in a polypeptide, together with antioxidants or scavengers of oxygen-derived free radicals (such as sulfhydryl containing compounds) or compounds that prevent the production of oxygen-derived free radicals (such as su peroxide dismutase), as it is known that oxygen-derived free radicals (such as su peroxide anion) can inactivate nitric oxide. Alternatively, or in addition, one can administer cofactors required for NO synthase activity, such as calcium, calmodulin, NADPH and/or tetrahydrobiopterin.

Alternatively, one can enhance, either in conjunction with the enhancement of precursors to nitric oxides or independently, components of the nitric oxide metabolic pathway. For example, one can enhance the amount of nitric oxide synthase present in the vessel wall, particularly at the site of lesions. This can be done by local administration to the lesion site or systemically into the vascular system. The synthase can be administered using liposomes, slow release particles, or in the form of a depot, e.g. in collagen, hyaluronic acid, biocompatible gels, vascular stents, or other means, which will provide the desired concentration of the NO synthase at the lesion site.

Instead of providing for the enhancement of NO at the physiological site of interest, one can choose to extend the lifetime of the signal transduced as a result of the presence of nitric oxide. Since cGMP is produced intracellularly as a result of a nitric oxide induced signal, employing agents which result in the production of or extending the lifetime of cGMP can be employed. Illustrative agents include cGMP phosphodiesterase inhibitors or agents which increase the amount of guanylate cyclase. Alternatively, one can intervene at the level of protein kinase C phosphorylation to provide the desired relaxation signal.

Alternatively, cells can be genetically engineered to provide for constitutive or inducible expression of one or more genes, which will provide for the desired relaxation response, by expressing NO synthase, or other enzyme or protein which is secreted and act extracellularly. Thus, expression vectors (viral or plasmid) can be prepared which contain the appropriate gene(s) and which can be introduced into host cells which will then produce high concentrations of nitric oxide or other intermediate in the relaxation pathway. These cells can be introduced at the lesion site or at another site in the host, where the expression will induce the appropriate response as to relaxation, proliferation, etc. The NO synthase or cells expressing the NO synthase can be present as depots by encapsulation and positioning at the site of interest. For example, porous stents can be produced which encapsulate the enzyme or cells to protect the enzyme from degradation or being washed away and, in addition, for the cells, to protect the cells from the immune system.

Cultured cells can be transfected with expression vectors containing the NO synthase or other gene ex-vivo and then introduced into the vessel wall, using various intra-arterial or intra-venous catheter delivery systems. Alternatively, techniques of in vivo gene transfer can be employed to transfect vascular cells within the intact vessel in vivo. The gene(s) can be expressed at high constitutive levels or can be linked to an inducible promoter (which can have tissue specificity) to allow for regulation of expression.

DNA constructs are prepared, where the appropriate gene, e.g. a NO synthase gene, is joined to an appropriate promoter, either with its native termination region or a different termination region, which can provide for enhanced stability of the messenger RNA. Constitutive promoters of particular interest will come from viruses, such as Simian virus, papilloma virus, adenovirus, HIV, Rous sarcoma virus, cytomegalovirus or the like, where the promoters include promoters for early or late genes, or long terminal repeats. Endogenous promoters can include the $\beta$-actin promoter, or cell-type specific promoters.

A construct is prepared in accordance with conventional techniques, the various DNA fragments being introduced into an appropriate plasmid or viral vector, normally a vector capable of replication in a bacterial and/or eucaryotic host. Normally, the vector will include a marker, which allows for selection of cells carrying the vector, e.g. antibiotic resistance. The vector will normally also include an origin which is functional in the host for replication. Other functional elements can also be present in the vector.

Once the vector has been prepared and replicated, it can then be used for introduction into host cells. The plasmid vector construct can be further modified by being joined to viral elements which allow for ease of transfection, can provide a marker for selection, e.g. antibiotic resistance, or other functional elements. Introduction of the plasmid vector construct into the host cells can be achieved by calcium phosphate precipitated DNA, transfection, electroporation, fusion, lipofection, viral capsid-mediated transfer, or the like. Alternatively, the expression construct within viral vectors can be introduced by standard infection techniques. For somatic cell gene therapy, autologous cells will generally be employed, although in some instances allogeneic cells or recombinantly modified cells can be employed. Usually the cells employed for genetic modification will be mature endothelial or vascular smooth muscle cells. Occasionally, the cells employed for genetic modification will be progenitor cells, particularly early progenitor cells. For example, myoblasts can be employed for muscle cells or hematopoietic stem cells or high proliferative potential cells can be employed for lymphoid and/or myelomonocytic cells.

Depending upon the nature of the cells, they can be injected into tissue of the same or different cellular nature, they can be injected into the vascular system, where they may remain as mobile cells or home to a particular site (i.e. the lesion). For the NO synthase gene, the number of cells which are administered will depend upon the nature of the cells, the level of production of the NO synthase, the desired level of NO synthase in the host vascular system, at the lesion site, or the like, whether the enhanced level of NO synthase is the only treatment or is used in conjunction with other components of the nitric oxide synthetic pathway, and the like. Therefore, the particular number of cells to be employed will be determined empirically in accordance with the requirements of the particular patient.

These cells can also be introduced into the circulation by first growing them on the surface of standard vascular graft material (i.e. Dacron or polytetrafluoroethylene grafts) or other synthetic vascular conduits or vascular bioprostheses.

Alternatively, one can use viral vectors, which are capable of infecting cells in vivo, such as adenovirus or retroviruses. In this case, the viral vector containing the NO synthase gene or other gene involved with the relaxation pathway will be administered directly to the site of interest, where it will enter into a number of cells and become integrated into the cell genome. Thus, one can titer the desired level of nitric oxide synthase which is secreted or other protein which is expressed, by providing for one or more administrations of the virus, thus incrementally increasing the amount of synthase which is secreted or other protein which is produced.

Alternatively, one can use modified liposomes as a vehicle for endovascular administration of the vector containing the NO synthase or other gene. One such modified liposome technique involves mixing the liposomes with the vector containing NO synthase. Once the gene expression construct-containing vector is incorporated into the liposome, the liposomes are coated with a protein (e.g. the viral coat protein of the Hemagglutinating Virus of Japan) that increases the affinity of the liposome for the vessel wall.

In some situations, the NO synthase or other gene in the relaxation pathway can be co-transfected with an artificial gene encoding an arginine rich polypeptide susceptible to proteolytic cleavage as an intracellular source of L-arginine. In other situations, the NO synthase or other gene can be co-transfected with the superoxide dismutase gene, so as to inhibit the degradation of the nitric oxide.

In some situations, acute treatment may be involved, requiring one or a few administrations. This will normally be associated with compounds which can act as nitric oxide precursors and are other than naturally occurring compounds or are compounds which can be added with naturally occurring compounds to enhance the rate of formation of nitric oxide. Thus, one can provide for acute administration of L-arginine and superoxide dismutase to increase the nitric oxide concentration over a restricted period of time. These administrations can be independent of or in conjunction with long term regimens.

The following examples are offered by way of illustration and not by way of limitation.

EXPERIMENTAL

EXAMPLE 1
Anti-atherogenic Effects of Oral Arginine

Study design: (See, Cooke et al., 1992, supra) Male New Zealand white rabbits (n=49) were assigned to one of three treatment groups: 10 were fed with normal rabbit chow for ten weeks (Control); 19 received chow enriched with 1% cholesterol (Chol); and 20 received a 1% cholesterol diet supplemented with 2.5% L-arginine hydrochloride in the drinking water (Arg.). Following ten weeks of the dietary intervention, animals were lightly sedated and the central ear artery cannulated for measurement of intra-arterial blood pressure, followed by collection of blood samples for serum chemistries and plasma arginine. Subsequently the animals were sacrificed and the left main coronary artery and the thoracic aorta were harvested for studies of vascular reactivity and histomorphometry. In some animals, blood was collected for studies of platelet and monocyte reactivity.

Results: Biochemical and physiological measurements. Hypercholesterolemic animals maintained on oral L-arginine supplementation (Arg) experienced a twofold elevation in plasma arginine levels in comparison to animals on a normal (Control) or 1% cholesterol (Chol) diet alone; the elevation in plasma arginine was maintained throughout the course of the study. Serum cholesterol measurements were elevated equally in both groups receiving the 1% cholesterol diet [50±6 vs. 1629±422 vs. 1852±356 mg/dl respectively for Control (=10), Chol (=13), and Arg (=14)]. There were no significant differences in hemodynamic measurements between groups.

Organ chamber studies of isolated vessels: For NO-independent responses, there were no differences between the treatment groups in maximal response or sensitivity to norepinephrine (a vasoconstrictor), or to nitroglycerin (a nitrovasodilator). By contrast, NO-dependent relaxations were attenuated in vessels harvested from hypercholesterolemic animals with a reduction in the maximal response to acetylcholine, and a reduction in sensitivity to calcium ionophore. In comparison, vessels harvested from hypercholesterolemic animals receiving L-arginine supplementation had improved NO-dependent relaxation. Similarly, sensitivity of vessels to calcium ionophore A23187 was greater in the Arg group. In a separate study, the effect of chronic arginine supplementation to improve NO-dependent relaxation was confirmed in the hypercholesterolemic rabbit abdominal aorta.

Histomorphometric studies (planimetry of EVG-stained sections): A blinded histomorphometric analysis revealed that medial cross-sectional areas of thoracic aortae were not different between the groups. By contrast, the intimal cross-sectional area (i.e. amount of atherosclerotic plaque) of vessels from hypercholesterolemic animals receiving L-arginine supplementation was reduced in comparison to those from animals receiving cholesterol diet alone. In the Arg animals the reduction in the intimal lesion was most pronounced in the ascending thoracic aorta and left main coronary artery. In the left main coronary artery of hypercholesterolemic animals receiving arginine, essentially no atherosclerotic plaque developed.

Changes in lesion surface area: In a second series of studies, the extent of the thoracic aorta involved by lesions was examined. In hypercholesterolemic rabbits receiving vehicle (n=6) or L-arginine supplement (n=6), thoracic aortae (from left subclavian artery to diaphragm) were harvested after ten weeks of treatment, bisected longitudinally, and stained with oil-red O. Vessels were photographed and vessel and lesion surface area determined by planimetry. Approximately 40% of the total surface area was covered with plaque in thoracic aortae from hypercholesterolemic animals receiving vehicle, whereas in thoracic aortae from arginine-treated hypercholesterolemic animals, less than 10% of the surface area was covered with plaque.

To summarize, dietary arginine supplementation increases plasma arginine levels, but does not alter serum cholesterol. This is associated with significant improvement in NO-dependent vasodilation as judged by bioassay. Finally, the improvement in NO-dependent vasodilation is associated with reduction in thickness and area of the lesions in vessels from hypercholesterolemic animals.

EXAMPLE 2
Inhibition of Platelet Aggregation by Oral L-arginine

The effect of L-arginine supplementation on platelet reactivity in rabbits that had normal chow (Control; n=6), a 1% cholesterol diet (Chol; n=5), or a 1% cholesterol diet supplemented with oral arginine (Arg; n=6), as detailed above, was examined. Arterial blood obtained after central ear artery cannulation was anticoagulated with 13 mM sodium citrate. Platelet-rich suspension was prepared by washing platelets in calcium-free Krebs-Henseleit solution and resuspending them in Tyrode's solution with albumin. The platelet count was adjusted at $2.5 \times 10^4$ platelets/$\mu$l by addition of platelet-poor plasma. Aggregation was initiated by addition of adenosine diphosphate and monitored by standard nephelometric techniques. In platelets derived from Chol animals, aggregation was not different in rate or maximum extent in comparison to platelets from Control animals (A). By contrast, aggregation of platelets from Arg animals was reduced by 50% (B).

Figure 2:
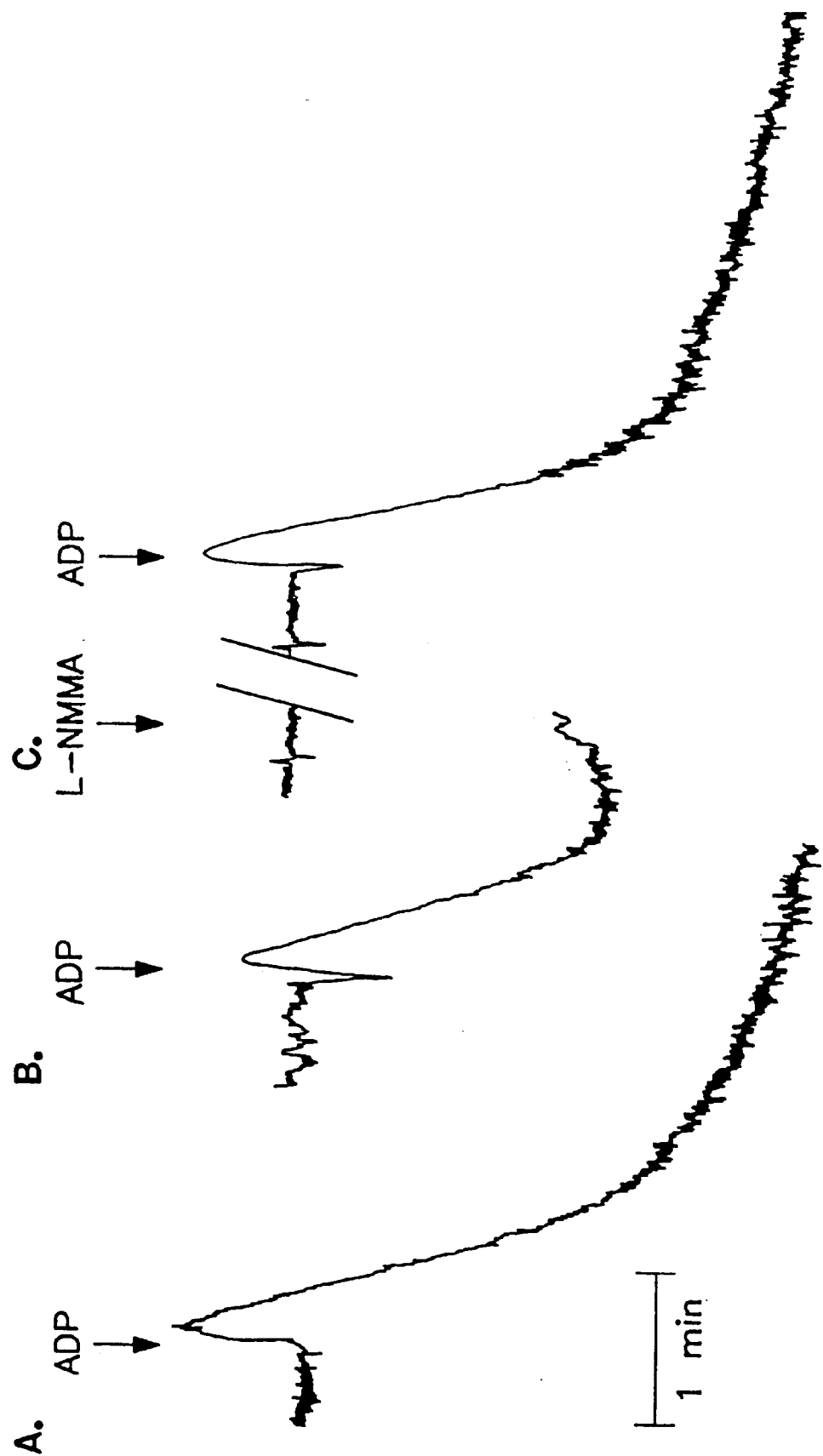
FIG. 2 is a nephelometric scan of the effect of L-arginine diet supplement on platelet reactivity as evidenced by platelet aggregation initiated by adenosine diphosphate (See Ex. 2)

This reduction in platelet aggregation was associated with a two-fold greater cGMP content in aggregated platelets from arginine-treated animals. The reduction of platelet reactivity could be reversed by administration of N-methylarginine ($10^{-4}$M) in vitro (C) (FIG. 2.) Therefore, the anti-platelet effect of chronic oral arginine administration can be credited to an increased synthesis of endogenous NO. Furthermore, NO synthesis may be induced in both the platelets and the endothelium.

EXAMPLE 3
Inhibition of Monocyte Adherence

A. Functional Binding Assay

To determine if oral arginine supplementation affects monocyte adherence, blood was collected from rabbits fed normal chow (=6) a 1% cholesterol diet (=6), or a 1% cholesterol diet supplemented with L-arginine (=6), as described above. Mononuclear cells were purified from blood by Ficoll-paque density gradient centrifugation. In these preliminary studies, adhesion was examined of blood leukocytes to a transformed endothelial cell line, bEnd3 (mouse brain-derived polyoma middle T antigen transformed endothelial cells). The Bend3 cells display the morphology of endothelial cells, and like human endothelial cells are capable of uptake of acetylated low-density lipoprotein and express adhesion molecules in a cytokine-regulatable fashion. Cultured cells were grown to confluence in 0.5 $cm^2$ Lab-Tek chamber slides (MilesScientific) and treated with control medium or with LPS (1 mg/ml) or TNFα (25 U/ml) for 18 hours. Cultures were washed with fresh assay buffer, and low, medium, or high concentrations of leukocytes (0.75, 1.5, or $3\times10^5$ cells/ml, respectively) were added per well. Following a 30-minute incubation on a rocking platform at room temperature to allow binding, the slides were inverted and immersed in buffer containing 2% (v/v) glutaraldehyde, such that non-adherent cells were lost and adherent cells were fixed to the monolayer. The adherent mononuclear cells were enumerated using video-light microscopy.

Monocytes from hypercholesterolemic animals (Chol) exhibited greater adherence, consistent with observation by others, that monocytes from hypercholesterolemic cats or humans exhibit greater adherence to cultured endothelial cells. (deGruijter, et al. (1991) Metabol. Clin. Exp. 40, 1119–1121; Fan, et al. (1991) Virchows Arch. B Cell Pathol. 61, 19–27).

In comparison to monocytes derived from vehicle-treated hypercholesterolemic animals (Chol), those from arginine-treated hypercholesterolemic animals (Arg) were much less adherent. This data shows that the arginine treatment inhibits adhesion of monocytes to the endothelium, which is the first observable event in atherogenesis.

EXAMPLE 4
Dietary L-Arginine Inhibits the Enhanced Endothelial-Monocyte Interaction in Hypercholesterolemia The earliest observable abnormality of the vessel wall in hypercholesterolemic animals is enhanced monocyte adherence to the endothelium, which occurs within one week of a high cholesterol diet. This event is thought to be mediated by the surface expression of endothelial adhesion molecules and chemotactic proteins induced by hypercholesterolemia. Another endothelial alteration that occurs in parallel is a reduced activity of nitric oxide (i.e., NO), derived from metabolism of L-arginine. As shown above chronic dietary supplementation with L-arginine restores NO-dependent vasodilatation in hypercholesterolemic rabbits, and that this improvement in No activity is associated with a striking anti-atherogenic effect. In the following study was tested the hypothesis that the anti-atherogenic effect of dietary arginine was mediated by endothelial derived NO which inhibits monocyte-endothelial cell interaction.

Methods

Animals. Male New Zealand White rabbits were pair fed, receiving one of the following dietary interventions for 2 weeks: normal rabbit chow (Cont, n=7); rabbit chow enriched with 1% cholesterol (Chol, n=7); or 1% cholesterol chow supplemented with 2.25% L-arginine HCl in the drinking water (Arg, n=7) ad libitum throughout the course of the study. In a second series of studies designed to further explore the role of endogenous NO on monocyte-endothelial cell interaction, another group of animals were pair fed, receiving a normal rabbit diet supplemented with either vehicle control (N=5) or the NO synthase antagonist, nitro-L-arginine (L-NA, 10 mg/100 ml; n=5), administered in the drinking water ad libitum throughout the course of the study (for an average daily dose of 13.5 mg/kg/day). In a third series of experiments animals received a normal diet and either vehicle (n=4), L-NA (13.5 mg/kg/day; n=4), or L-NA and hydralazine (n=4) added to the drinking water for two weeks. At this dose, hydralazine (5 mg/kg/day) reversed the increase in blood pressure induced by L-NA. One day before sacrifice (after 2 weeks of dietary intervention), animals were lightly sedated and the central ear artery was cannulated for collection of blood samples.

Mononuclear cell culture and isolation. Murine monocytoid cells, WEHI 78/24 cells were grown in Dulbecco's Modified Eagle's Medium supplemented 10% fetal calf serum (vol/vol) and were kept in an atmosphere of 5% $co_2$/95% air. Prior to binding studies, mononuclear cells were fluorescently labeled with TRITC (3 μg/ml). To confirm the results using WEHI cells, in some studies binding studies were performed in parallel using rabbit mononuclear cells. Mononuclear cells were isolated from fresh whole blood of Control rabbits before sacrifice.

Preparation of aortic endothelium and binding assay. After 2 weeks of the dietery intervention, the thoracic aortae were removed and placed in cold, oxygenated saline. A 15 mm segment of thoracic aorta was excised from a point immediately distal to the left subclavian artery to the mid-thoracic aorta. The segments were then carefully opened longitudinally and placed into culture dishes containing HBSS medium. Aortic strips were fixed to the culture dish using 25 gauge needles so as to expose the endothelial surface to the medium. Culture dishes were then placed on a rocking platform at room temperature.

After 10 minutes the HBSS medium was replaced by binding medium containing WEHI cells. The aortic strips were incubated with the mononuclear cells for 30 minutes. The medium was then replaced by fresh binding medium without cells to remove non-adherent cells. The aortic segments were then removed and placed on a glass slide, and adherent cells counted under epifluorescent microscopy from at least 30 sites on each segment.

Results

Figure 3:
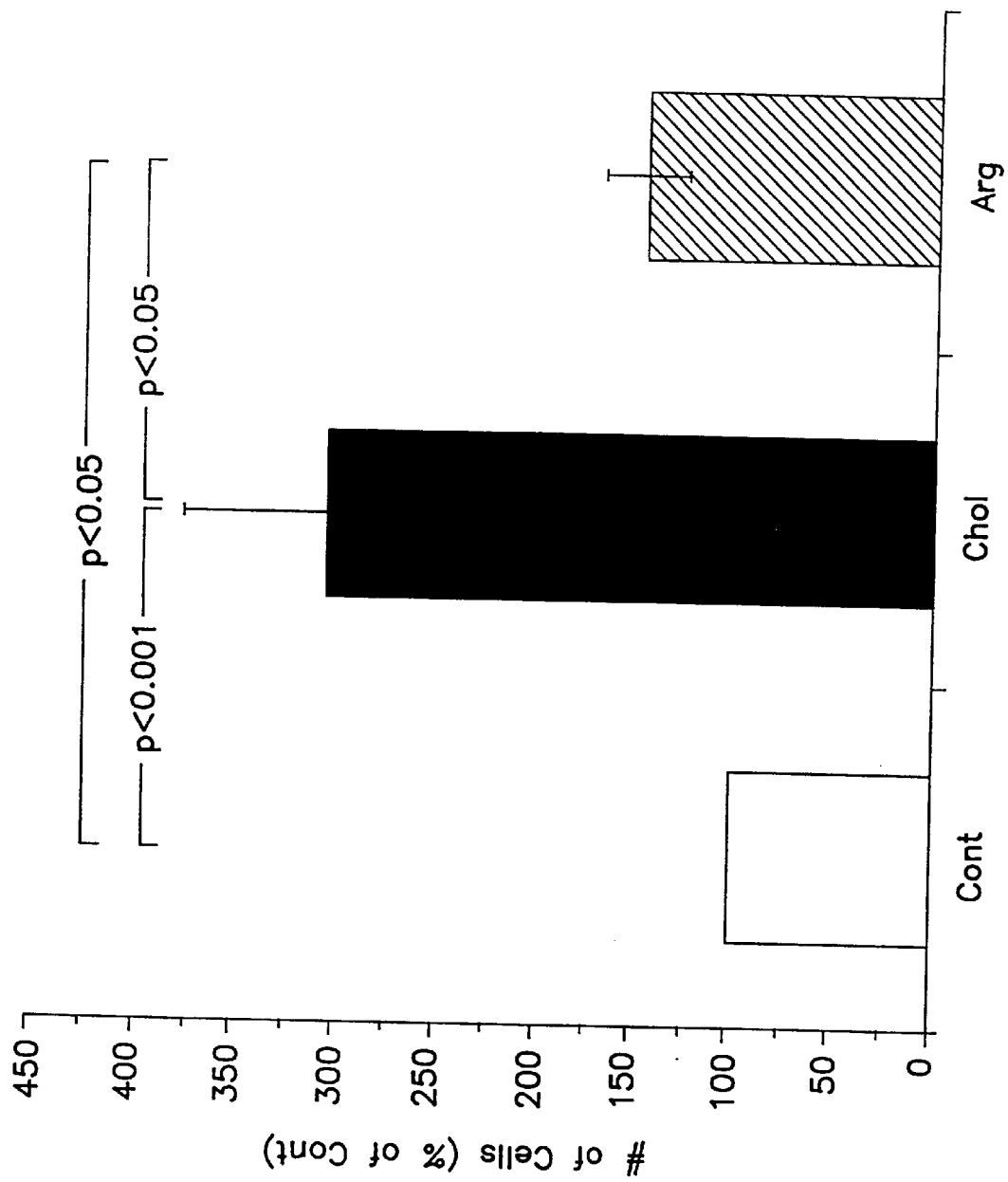
FIG. 3 is a bar diagram comparing the effect of L-arginine diet supplement on cell binding to aortic endothelium of hypercholesterolemic animals (See Ex. 4)

Monocyte adhesion to rabbit aortic endothelium. Exposure of WEHI 78/24 cells to normal rabbit aortic endothelium results in a minimal cell binding in this ex vivo adhesion assay. However, when WEHI cells were incubated with aortic endothelium from hypercholesterolemic animals (Chol; n=7), cell binding was enhanced 3-fold in comparison to Cont (n=7). The increased cell binding manifested by aortic endothelium of hypercholesterolemic animals was significantly attenuated by L-arginine supplementation (n=7). (FIG. 3) Similar results were achieved when adhesion assays were performed in parallel with mononuclear cells that were freshly isolated from Cont animals (n=2) in each of the three groups.

Effect of chronic NO synthase inhibition on endothelial adhesiveness. To further investigate the role of endothelium-derived NO in modulating endothelial-monocyte interaction, an additional series of binding studies were performed using thoracic aorta from animals that received regular chow supplemented with vehicle (n=5) or the NO synthase inhibitor, L-NA (n=5). The adhesion of WEHI cells was markedly increased when incubated with aortic endothelium from L-NA animals compared to control endothelium. This effect could not be attributed to hypertension caused by L-NA since concomittant administration of hydralazine normalized blood pressure but did not reverse the augmentation of cell binding induced by L-NA.

In a separate series of studies it was confirmed that chronic administration of L-NA (the inhibitor of NO synthase) significantly inhibited generation and release of NO from the vessel wall (as measured by chemiluminescence), compared to vessels from animals treated with vehicle or arginine.

The salient findings of this investigation are: 1) monocyte binding to the endothelium ex vivo is increased in vessels from hypercholesterolemic animals; 2) this increase in monocyte binding is attenuated in hypercholesterolemic animals treated chronically with the NO precursor L-arginine; 3) monocyte binding to the endothelium is increased in vessels from normocholesterolemic animals treated with the NO synthase antagonist L-nitro-arginine; and 4) this effect of NO synthase antagonism was not reversed by administration of hydralazine in doses sufficient to normalize blood pressure. These findings are consistent with the hypothesis that NO inhibits monocyte-endothelial cell interaction.

To conclude, an ex vivo model of monocyte binding has been used to study the increase in endothelial adhesiveness induced by hypercholesterolemia. Endothelial adhesiveness is attenuated by oral administration of the NO precursor L-arginine is shown. Conversely, inhibition of NO synthase activity by oral administration of nitro-arginine strikingly increases endothelial affinity for monocytes in vitro. The data are consistent with NO being an endogenous anti-atherogenic molecule.

EXAMPLE 5
Effect of NO Synthase Expression on Proliferation of Vascular Smooth Muscle Cells Cultured rat aortic vascular smooth muscle cells under confluent quiescent conditions were studied. An efficient viral coat protein-mediated DNA transfer method was employed to transfect the cells with the NO synthase gene driven by the β-actin promoter and CMV enhancer. This resulted in increased NO synthase activity (as measured by the arginine-to-citrulline conversion assay) in comparison to control vector transfected cells. Transfection of the NO synthase gene completely abolished serum-stimulated DNA synthesis compared to control vector transfection. These results indicated that increased expression of NO synthase (associated with increased production of NO) inhibits excessive proliferation of vascular smooth muscle cells. This inhibition can be correlated with treatment of atherosclerosis and restenosis.

EXAMPLE 6
Gene Therapy Using NO Synthase cDNA Prevents Restenosis

The study in Example 5 indicated that NO inhibits proliferation of vascular smooth muscle cells. In atherogenesis and restenosis, excessive proliferation of vascular smooth muscle cells contributes to lesion formation. Injury to the endothelium in atherosclerosis and after catheter interventions apparently reduces or removes the salutary influence of NO. The following study shows delivery of the gene for NO synthase to the vessel wall inhibits lesion formation.

A plasmid construct encoding the cDNA of endothelial-type NO synthase (EC-NOS) was synthesized. A full length cDNA encoding for EC-NOS was inserted into the EcoRI site of the pUCcaggs expression vector. Balloon angioplasties of the carotid artery in Sprague-Dawley rats were performed and HVJ-liposomes with plasmids encoding EC-NOS cDNA infused, or plasmids lacking EC-NOS cDNA (control vector) infused. After 4 days to 2 weeks, the rats were sacrificed and the carotid arteries harvested for: 1) histomorphometry; 2) measurement of DNA synthesis; and 3) ex vivo determination of NO synthesis and release by bioassay and by chemiluminescence.

Results

Figure 4:
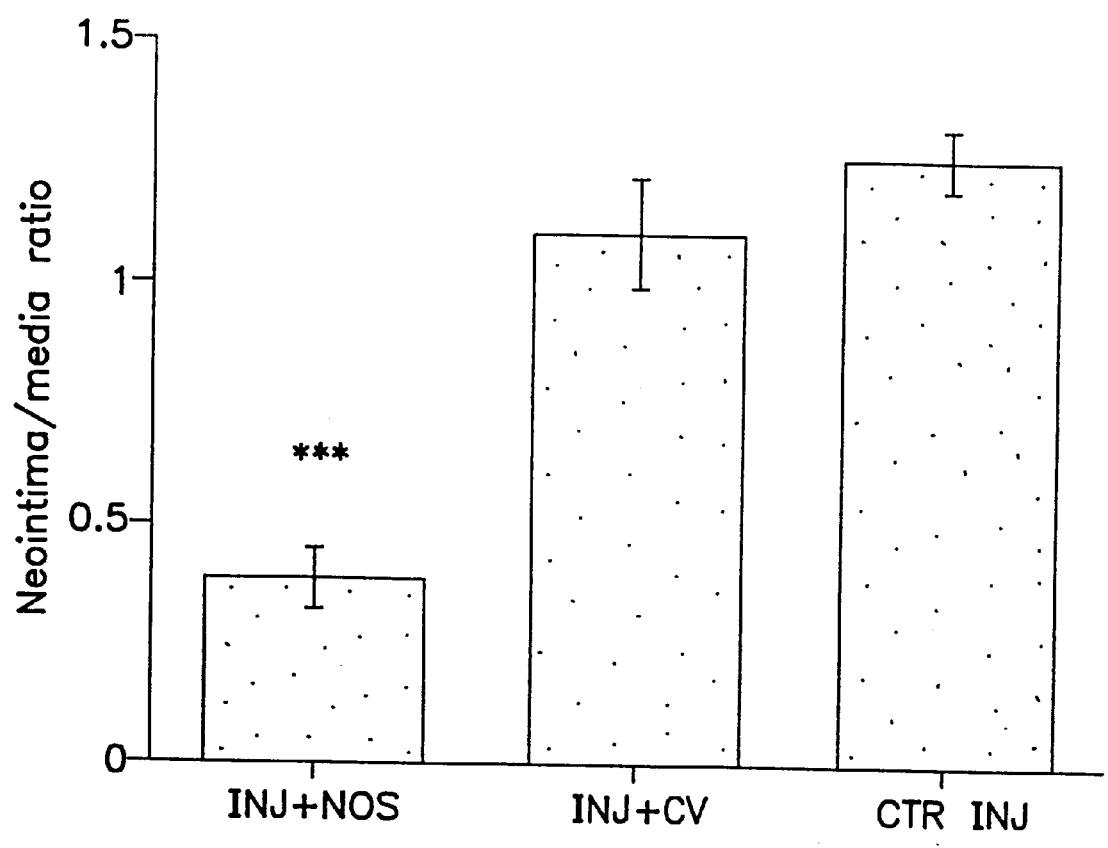
FIG. 4 is a bar diagram of morphometric measurements of intimal lesion thickness in EC-NOS treated animals in comparison to control vector or untreated injured vessels (See Ex. 6)
Figure 5:
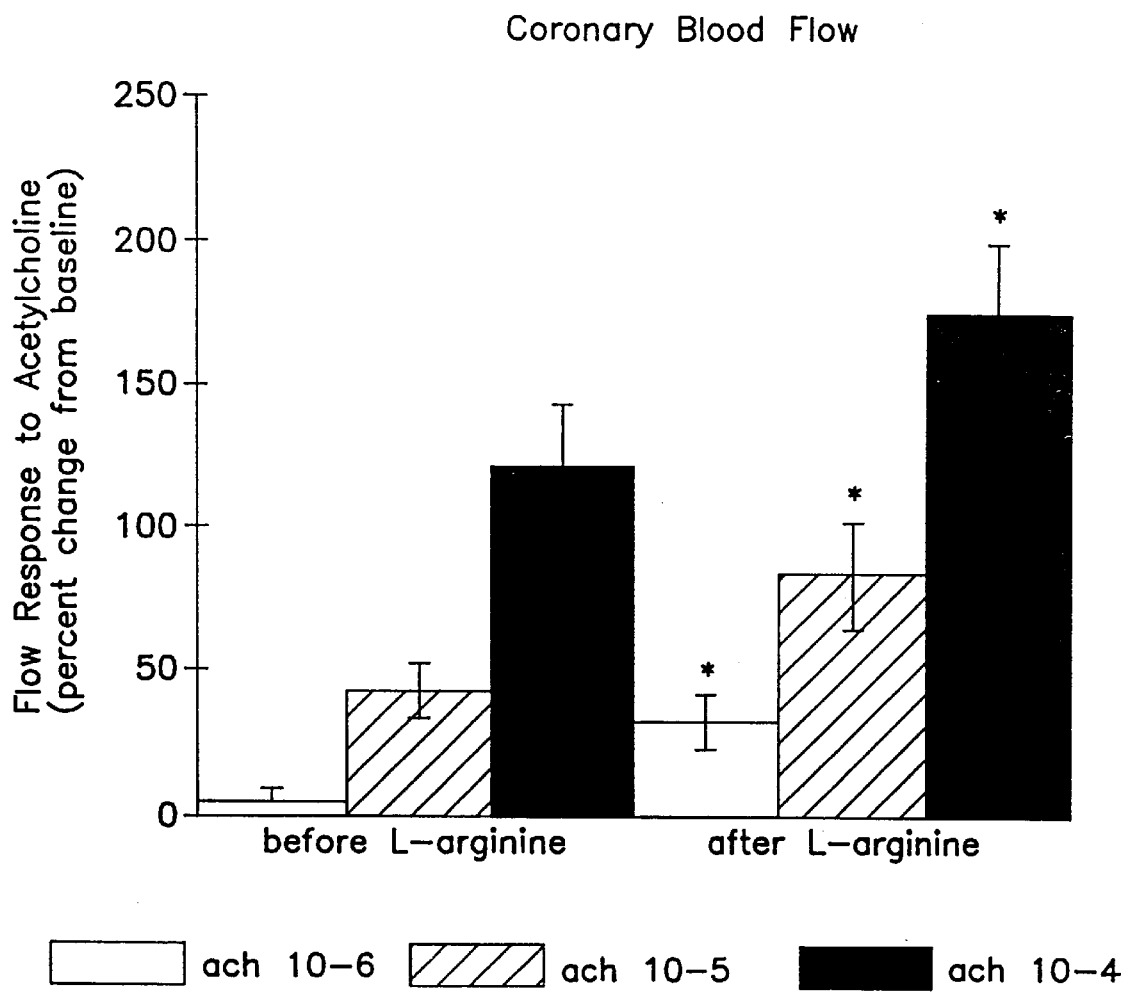
FIG. 5 is a bar graph showing increases in coronary blood flow in response to intracoronary infusions of acetylcholine (ACH) before and after intravenous infusion of L-arginine (10 g), in patients with transplant atherosclerosis. Acetylcholine stimulates the release of NO from the vessel wall causing vasodilation and increased blood flow. There is improved NO-dependent vasodilation after L-arginine administration.
Figure 6:
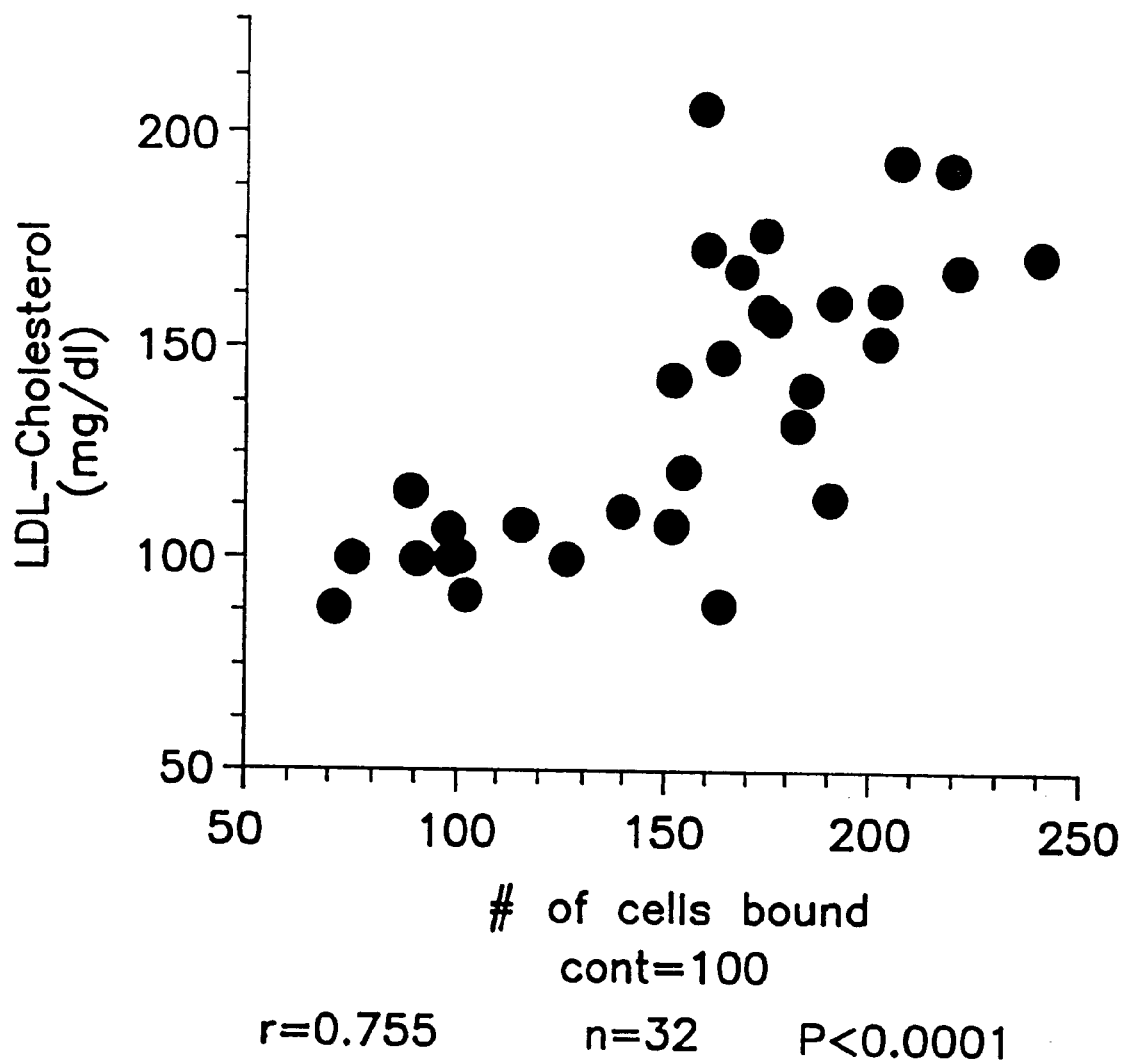
FIG. 6 is a scatter-diagram illustrating the relationship between the level of blood LDL-cholesterol and monocyte binding. Monocytes were isolated from the blood of humans with normal or elevated cholesterol levels. The binding of these monocytes to endothelial cells in culture was observed. Monocytes from individuals with high cholesterol levels have a greater adhesiveness for endothelial cells. This monocyte-endothelial cell interaction in vivo is the first step in the development of atherosclerotic plaque.
Figure 7:
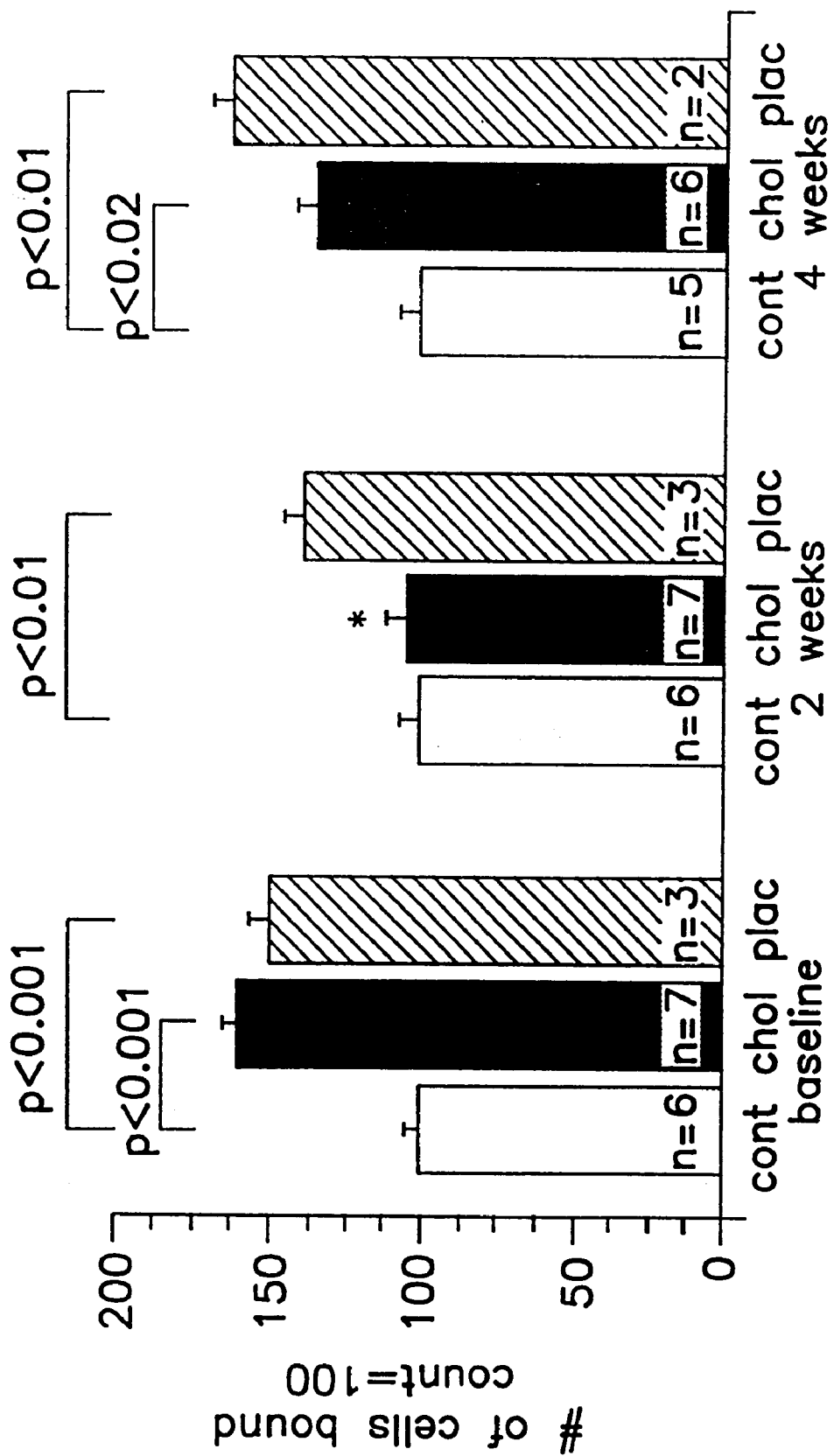
FIG. 7 is a bar diagram showing the adhesiveness of monocytes obtained from subjects with normal cholesterol levels (CONT) and those from hypercholesterolemic (HC) humans, before, during, and after treatment with arginine (the NO precursor). Prior to initiating arginine (Arg) or placebo (plac) treatment, monocytes from hypercholesterolemic individuals have a greater tendency to bind to endothelial cells ex vivo (baseline). After 2 weeks of arginine treatment monocytes from these hypercholesterolemic individuals have a significantly reduced adhesiveness and are no different from those of the normal subjects. At this point arginine therapy was discontinued and there was a washout (4 weeks). At this time point, monocytes from the patients previously treated with arginine now have increased adhesiveness, off of the arginine treatment.
Figure 8:
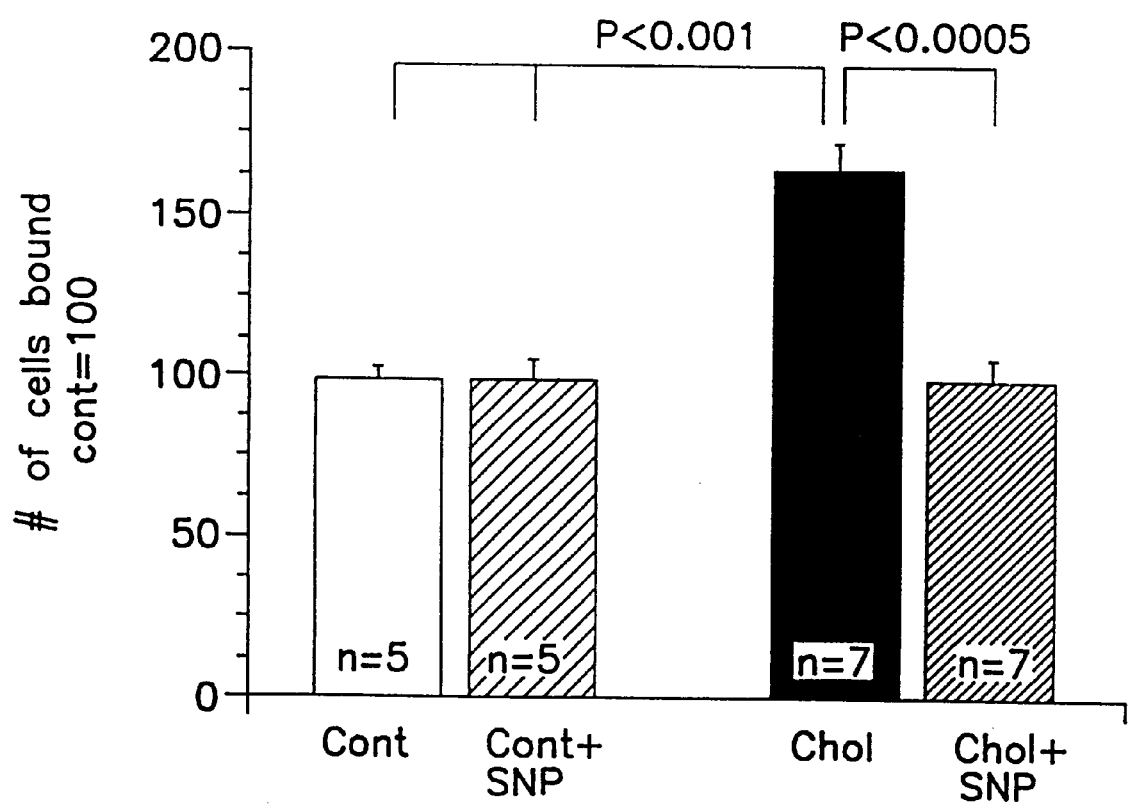
FIG. 8 is a bar diagram which shows that monocytes from individuals with elevated cholesterol (CHOL) have greater adhesiveness for endothelial cells. However, after treatment with sodium nitroprusside (CHOL +SNP), the adhesiveness of these monocytes is normalized. SNP is an NO donor.
Figure 9:
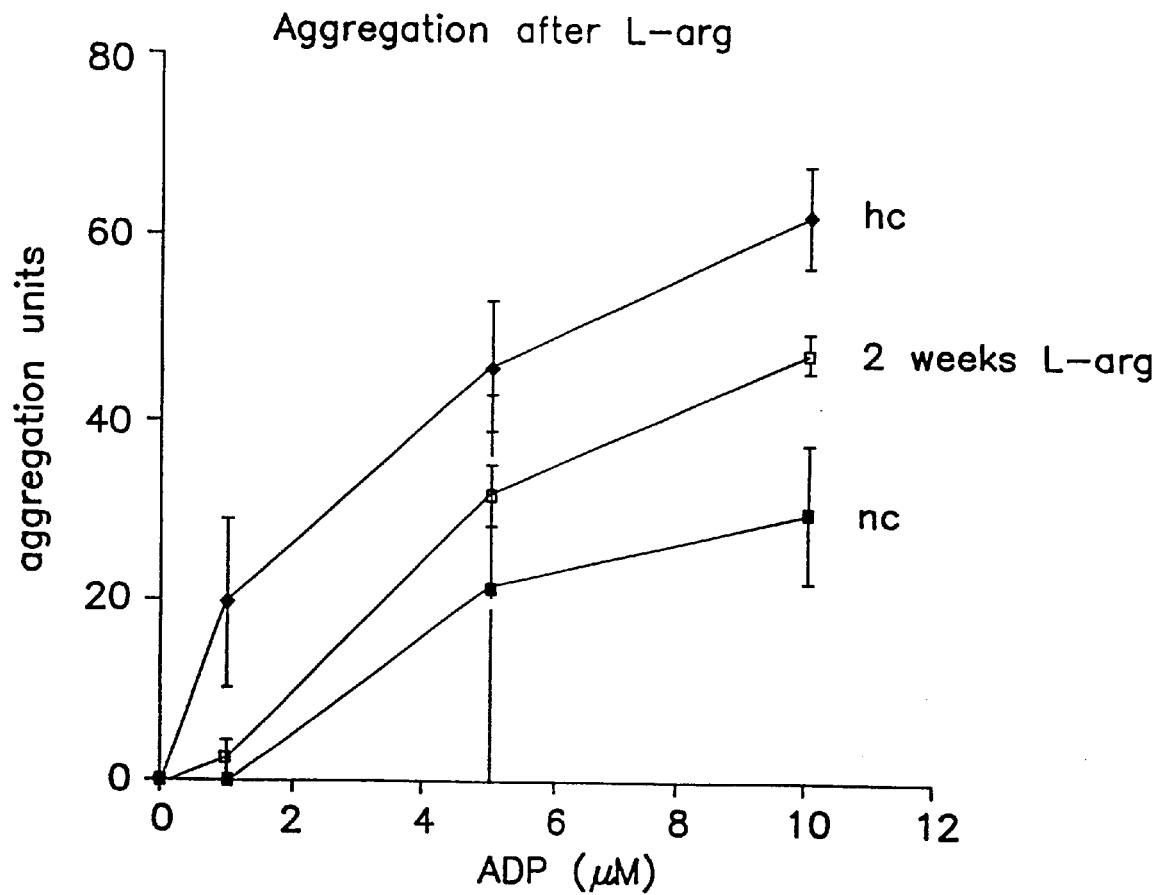
FIG. 9 is a set of dose response curves showing aggregation of platelets obtained in hypercholesterolemic humans (hc), hypercholesterolemic individuals receiving oral L-arginine (hc;L-arg), and individuals with normal cholesterol levels (nc). Platelet aggregation ex vivo in response to adenosine diphosphate (ADP) is increased in hc individuals in comparison to normal individuals. After 2 weeks of treatment with oral L-arginine, platelet aggregation is attenuated in the hypercholesterolemic individuals.

Morphometric measurements 2 weeks after injury revealed a significant (68%) reduction of intimal lesion thickness in EC-NOS treated (Inj+NOS) in comparison to control vector treated (Inj+CV) or untreated (Ctr Inj) injured vessels. (FIG. 4) Measurements of DNA synthesis were performed 4 days after injury using bromodeoxy-uridine. EC-NOS transfection significantly limited bromodeoxyuridine incorporation (by 25%) in comparison to control vector treated or untreated injured vessels. Vessel segments were studied ex vivo using organ chamber technique to bioassay for NO release. Calcium ionophore increases intracellular calcium and activates NO synthase to produce NO. Calcium ionophore induced relaxations in injured carotid arteries transfected with control vector that were only 15% of uninjured vessels. Injured arteries that had been transfected with EC-NOS relaxed to a much greater degree, approximately 50% of that observed in uninjured vessels. Direct measurement of NO (by chemiluminescence) released into the medium revealed that NO released by injured tissues (transfected with the control vector) was only 20% of that released by normal uninjured tissues. By contrast, injured tissues transfected with EC-NOS released more NO (about 75% of normal).

To conclude, balloon angioplasty of the rat carotid artery removes the endothelial source of NO, induces excessive vascular smooth muscle DNA synthesis and proliferation, resulting in an intimal lesion (restenosis). Transfection of the vessel with EC-NOS at the time of balloon injury partially restores NO production by the vessel, and this is associated with reduced DNA synthesis and vascular smooth muscle proliferation, thereby reducing lesion formation. These results are consistent with the conclusion that NO is an endogenous anti-atherogenic molecule.

EXAMPLE 7
Exclusion of the Effect of Enhanced Nitrogen or Caloric Balance as Causing the Observed Results To exclude an effect of L-arginine on nitrogen or caloric balance as the cause of these results, six animals received 1% cholesterol diet supplemented by additional methionine to increase the dietary methionine six-fold. At ten weeks animals were sacrificed for studies of platelet and vascular reactivity, and histomorphometry. Endothelium-dependent relaxation, platelet aggregation and intimal thickness were not different from those of animals fed 1% cholesterol diet alone. These results reveal that another amino acid, methionine (which is not a precursor of NO) does not mimic the effect of the amino acid L-arginine. Therefore it seems likely that the effect of L-arginine is due to its metabolism to nitric oxide, rather than some other effect of amino acid administration (i.e. change in nitrogen or caloric balance).

EXAMPLE 8

Oral L-arginine Normalizes Monocyte Adhesiveness in Hypercholesterolemic Humans

Adherence of monocytes to the endothelium is the first observable event in the development of atherosclerosis. We hypothesized that chronic oral administration of L-arginine to hypercholesterolemic humans would enhance the generation of endothelium-derived NO, and thereby inhibit the interaction of monocytes with the endothelium. In this investigation we have developed a reproducible assay for the binding of human monocytes to cultured endothelial cells, and we have examined the effect of hypercholesterolemia and L-arginine treatment on this interaction.

The control subject population in this study included 12 normal volunteers, (10 males and 2 females), with an average age of 37±2 yrs. Normalcy was determined by a careful history, physical examination, and laboratory analysis to exclude individuals with hematologic, renal, or hepatic dysfunction or clinically evident atherosclerosis. There were 20 patients (10 males and 10 females) with hypercholesterolemia as defined by a total plasma cholesterol greater than 240 mg/dl and a LDL cholesterol level greater than 160 mg/dl. These individuals had an average age of 51±2 yrs. None of the subjects were taking diuretics, vasoactive medications, antiplatelet or hypolipidemic medications. This study was approved by the Stanford University Administrative Panel on Human Subjects in Medical Research and each subject gave written informed consent before entry into the study. Blood was drawn from each subject in the postabsorptive state.

We isolated human monocytes from citrated venous blood. The blood was centrifuged and the buffy coat removed and resuspended with HBSS. The suspension was then carefully layered onto a cushion of 1.068-d Histopaque, and centrifuged. After centrifugation, the monocytes were aspirated.

We used the transformed endothelial cell (EC) line, bEnd3 to examine monocyte-endothelial binding ex vivo. The bEnd3 cells express endothelial adhesion molecules and bind monocytes in a cytokine-inducible fashion with kinetics similar to those observed with human umbilical vein endothelium. Monocytes were added to the wells containing the endothelial monolayers to reach a final cell number of $3\times10^6$/ml. In some studies, monocytes were exposed in vitro for 30 minutes to sodium nitroprusside (an NO donor) prior to the binding assay.

The six-well plates were transferred to a rocking platform and rocked for 30 minutes at room temperature. After 30 minutes, the cell suspension was aspirated from each well and wells were then rinsed with binding buffer to remove non-adherent monocytes. Videomicroscopic counting of adherent cells was performed using a computer aided image analysis system.

Results

Oral administration of L-arginine (7 g daily for 2 weeks) to hypercholesterolemic humans increased plasma arginine values by 60% (from 79±10 to 128±12 mM; n=7), whereas L-arginine values in the placebo-treated (n=3) and normocholesterolemic (n=6) groups remained unchanged. The administration of oral L-arginine had no effect on any of the biochemical or hematologic parameters and was well tolerated. Oral L-arginine did not lower total cholesterol or LDL cholesterol. Two patients dropped out of the study; one because he did not want to take the pills, and one because of reactivation of oral herpes during the study.

The results of the adhesion assays were highly reproducible. Monocytes derived from hypercholesterolemic individuals demonstrated a 50±8% increase in bound cells/hpf in comparison to cells from normal individuals (p<0.0001). The degree of adhesiveness was correlated to the plasma levels of LDL cholesterol (R=0.7, n=33; p<0.0001).

In an open-label study, 3 hypercholesterolemic individuals were treated with oral L-arginine supplementation for 2 weeks. Arginine treatment resulted in a 38% decrease in monocyte adhesiveness.

To confirm this effect of L-arginine treatment and to control for any experimental bias, a double-blinded, placebo-controlled, randomized study was performed. Ten hypercholesterolemic subjects were randomized (1:2) to placebo or L-arginine treatment; 6 normocholesterolemic individuals were studied in parallel to control for variation over time in the binding assay. At baseline, the adhesion of monocytes from both hypercholesterolemic groups was increased in comparison to the normocholesterolemic individuals (p<0.001). After 2 weeks of L-arginine administration, there was an absolute reduction of 53% in monocyte binding (n=7, p<0.005, baseline vs 2 weeks). By contrast, there was no significant change in the adhesiveness of monocytes isolated from hypercholesterolemic individuals treated with placebo. Two weeks after discontinuation of the L-arginine treatment, the adhesiveness of the monocytes isolated from hypercholesterolemic individuals had significantly increased compared to the normocholesterolemic individuals (34±9% increase in bound cells/hpf; p<0.05), and was also significantly increased in comparison to the binding obtained after 2 weeks of L-arginine therapy (an increase of 30±9%, p<0.05). The adhesiveness of monocytes from placebo-treated hypercholesterolemic individuals did not change significantly during the washout period.

In some studies monocytes were exposed to sodium nitroprusside or vehicle control for 30 minutes in vitro. Pre-incubation of the cells from hypercholesterolemic individuals with the NO donor sodium nitroprusside ($10^{-5}$M) markedly reduced binding (164±9% vs 98±7% vehicle vs sodium nitroprusside; n=7, p<0.0005; values expressed as a percent of the normocholesterolemic control exposed to vehicle).

To conclude, the salient findings of this investigation are that: 1) Hypercholesterolemia enhances the adhesiveness of monocytes for endothelial cells, 2) oral arginine supplementation reverses the increase in adhesiveness of monocytes from hypercholesterolemic individuals, and 3) the effect of oral arginine is mimicked in vitro by exposure of the monocytes from hypercholesterolemic individudals to sodium nitroprusside, an NO donor.

EXAMPLE 9

Platelet Hyperaggregability in Hypercholesterolemic Humans Reversal by Oral L-Arginine In this study we tested the hypothesis that chronic L-arginine supplementation would inhibit platelet reactivity in hypercholesterolemic humans. Venous blood was collected from normal (NC; n=11) and hypercholesterolemic (HC; n=22) volunteers for isolation of platelet-rich plasma and aggregometry. Half the HC group received L-arginine (7 g/d) for 2 weeks; aggregometry was performed using collagen (5 mg/ml) before and after 2 wks of treatment.

Results: HC platelets were hyperaggregable. After 2 wks of L-arginine, the aggregability of HC platelets was reduced.

These studies are consistent with our previous observations in animals that oral administration of L-arginine inhibits platelet reactivity.

EXAMPLE 10

Intravenous Administration of L-Arginine Improves Endothelium-dependent Vasodilation in Hypercholesterolemic Humans Hyperlipoproteinemia impairs endothelium-dependent vasodilation, even before the development of atherosclerosis. We hypothesized that administration of L-arginine may increase synthesis of NO and thereby improve endothelium-dependent vasodilation in hypercholesterolemia. Indeed, our earlier studies conducted in cholesterol-fed rabbits support this notion. The following data demonstrates that L-arginine augments endothelium-dependent vasodilation in forearm resistance vessels of hypercholesterolemic humans.

The control subject population in this study included 11 normal volunteers comprising (10 males and 1 female). Their ages ranged from 31 to 49 and averaged 39±2 yr. There were 14 patients with hypercholesterolemia. Hypercholesterolemia was defined as a serum LDL cholesterol level greater than the 75th percentile adjusted for age and sex. These individuals included 11 males and 3 females whose ages ranged from 22 to 48 and averaged 38±2 yr.

Alcohol, caffeine, and cigarettes were all prohibited within 12 h of the study. Under local anesthesia and sterile conditions, a polyethylene catheter was inserted into a brachial artery of each subject for determination of blood pressure and for infusion of drugs. A separate polyethylene catheter was inserted into the antecubital vein for infusion of L-arginine. Bilateral forearm blood flow was determined by venous occlusion strain gauge plethysmography, using calibrated mercury-in-silastic strain gauges, and expressed as ml/100 ml tissue per min.

To assess NO-dependent vasodilation, methacholine chloride (which induces the endothelium to release NO) was administered via the brachial artery. Forearm blood flow was measured during infusion of methacholine chloride at concentrations of 0.3, 3, and 10 $\mu$g/min each for 3 min.

After completion of the methacholine chloride infusions, all normal subjects and 10 individuals with hypercholesterolemia were given L-arginine intravenously over 30 minutes and then the methacholine infusions were repeated. D-arginine, the enantiomer of L-arginine, is not a precursor of NO. Thus, to ensure that any observed effects of L-arginine were due to its contribution to the synthesis of NO and not just secondary to its physiochemical properties, five individuals with hypercholesterolemia received D-arginine intravenously.

Results. Baseline blood pressure, heart rate, and forearm blood flow did not differ between normal and hypercholesterolemic subjects. Intraarterial infusion of methacholine chloride caused a dose-dependent increase in forearm blood flow. In the hypercholesterolemic subjects, however, cholinergic vasodilation was less than that of normal subjects ($p<0.05$). The maximal forearm blood flow response to methacholine in normal subjects is 19.0±1.9 ml/100 ml of tissue per min, and in hypercholesterolemic subjects, it was 13.7±1.7 ml/100 ml of tissue per min ($p<0.05$).

In the normal subjects, L-arginine did not potentiate the vasodilation that occurred during the administration of methacholine chloride. In the hypercholesterolemic subjects, however, the L-arginine infusion augmented the vasodilation to methacholine chloride by 25% ($p<0.05$). There were no complications or side-effects of the L-arginine infusions.

The important findings in this study are: (a) endothelium-dependent vasodilation (due to the release of NO) is reduced in forearm resistance vessels of hypercholesterolemic humans; and (b) intravenous administration of L-arginine improves endothelium-dependent vasodilation in these individuals. NO not only causes vasodilation, but it also inhibits platelet aggregation and suppresses monocyte adhesion.

EXAMPLE 11

Administration of Intravenous L-Arginine Improves Coronary Endothelial Function in Cardiac Transplant Recipients A reduction in coronary NO-dependent vasodilation occurs in cardiac transplant recipients and may represent an early marker for the development of graft atherosclerosis. Reduced NO-dependent vasodilation in response to acetylcholine is an indicator of endothelial dysfunction and has been attributed to reduced synthesis or accelerated degradation of endothelium-derived nitric oxide. We hypothesized that endothelial dysfunction of epicardial coronary arteries at an early stage of coronary allograft atherosclerosis might be reversed by L-arginine. The present study tested the hypothesis that administration of L-arginine, the precursor of endothelium-derived NO, improves endothelial vasodilator function of coronary conduit and resistance vessels.

Cardiac transplant recipients scheduled for elective annual coronary angiography at Stanford University hospital were screened for possible participation in the study. The study protocol was approved by the Stanford University Committee on Human Subjects in Medical Research. All patients gave written informed consent. Eighteen patients who had cardiac transplantation 1 to 13 years previously were studied.

Vasoactive medications were discontinued at least 12 hours before the study. After diagnostic angiography revealed no visually apparent coronary stenosis, a guiding catheter was used to cannulate the left main coronary artery. An infusion catheter was then advanced over a Doppler flow velocity guide wire into a nonbranching segment of the coronary artery for infusion of acetylcholine (which stimulates the endothelium to release NO). After baseline angiography was performed, increasing concentrations of acetylcholine were serially infused over 3 minutes. Infusion of acetylcholine continued until the maximum dose ($10^{-4}$ mol/L) was reached or until total coronary occlusion occurred. Then an intravenous infusion of L-arginine (10 g over 15 minutes) was performed. Thereafter, the intracoronary infusion of acetylcholine was repeated. Coronary angiography and Doppler flow velocity recording was performed at the end of the L-arginine infusion and after the infusion of each concentration of acetylcholine.

Results. In epicardial coronary arteries of these transplant recipients, acetylcholine caused vasoconstriction. Epicardial coronary vasoconstriction caused by acetylcholine was attenuated by infusion of L-arginine ($10^{-4}$ mol/L, −6.8% versus −2.8%; $p<0.01$). In coronary resistance vessels, acetylcholine induced vasodilation, reflected by increases in blood flow. The increase in coronary blood flow was significantly enhanced with L-arginine ($p<0.002$). There were no complications or side-effects of the L-arginine infusion.

The coronary vasculature of cardiac transplant recipients exhibits a generalized reduction of NO-dependent vasodilation. L-arginine improves endothelial-derived NO dependent vasodilation of both coronary microvasculature and epicardial coronary arteries.

It is evident from the above results, that by enhancing the nitric oxide levels, by means of nitric oxide precursor compounds or other compounds in the nitric oxide pathway, substantial benefits will ensue to patients with vascular degenerative diseases. This treatment will diminish the formation of atherosclerotic plaque and restenosis, by inhibiting adhesion of monocytes and platelets, and by reducing the proliferation of vascular smooth muscle cells.

By virtue of administering to the host, based on a predetermined regimen, or providing in the host a supply of a component in the synthetic pathway for production of nitric oxide, so as to maintain a mildly elevated level of nitric oxide in the host, particularly at the site to be treated, the incidence of plaque formation can be substantially diminished. This can be achieved in a variety of ways: by oral administration in accordance with a predetermined regimen of various compounds associated with nitric oxide formation, e.g. L-arginine; by administration at the site, in a predetermined regimen of compounds which can produce nitric oxide, either directly or as a result of physiologic action of endogenous compounds, e.g. enzymes; by employing combinations of compounds, which by their action result in the production of nitric oxide; or the like. These individual administrations, can be done independently or in conjunction with a regimen of other compounds associated with the production of nitric oxide.

Alternatively, one may use genetic engineering to introduce a gene associated with a component in the synthetic pathway for production of nitric oxide, e.g. nitric oxide synthase, where the enhanced production of such compounds will have the effect of driving the equilibrium to an enhanced production of nitric oxide. Thus, the subject invention provides a plurality of pathways to enhance the synthesis or action of nitric oxide, or reduce the degradation of nitric oxide, thereby increasing the effect of endogenous nitric oxide to prevent the formation of vascular lesions and to inhibit restenosis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting the development of atherosclerosis, restenosis or thrombosis in the vascular system of a human host susceptible to atherosclerosis, restenosis or thrombosis, said method comprising:

orally administering as a dietary supplement to said host in accordance with a predetermined regimen a prophylactic or therapeutic dose of an amino acid formulation consisting of a mixture of L-arginine and L-lysine, as the amino acids or their physiologically acceptable salts to enhance the level of endothelial NO in the vascular system to inhibit the development of atherosclerosis, restenosis or thrombosis or to reduce lesions associated with atherosclerosis.

2. A method of inhibiting the development of atherosclerosis or restenosis in the vascular system of a human host susceptible to said atherosclerosis or restenosis, said method comprising:

orally administering as a dietary supplement an amino acid formulation consisting of the amino acid L-arginine and its physiologically acceptable salts, in an amount sufficient to enhance the level of endothelial nitric oxide at a daily dosage in the range of 3 to 12 g per day, whereby cholesterol level is unaffected by said endothelial nitric oxide and the development of said atherosclerosis or restenosis is inhibited.

3. A method of inhibiting the development of the diseases atherosclerosis, restenosis or thrombosis in the vascular system of a human host susceptible to said diseases, said method comprising:

orally administering as a dietary supplement an amino acid mixture formulation consisting of a mixture of L-arginine and L-lysine, as the amino acids or their physiologically acceptable salts, in an amount sufficient to provide a plasma level of said amino acids of 0.2 to 30 mM, to enhance the level of endothelial nitric oxide, whereby the development of said diseases is inhibited.

4. A method of inhibiting the development of restenosis in the vascular system of a human host susceptible to said restenosis, said method comprising:

orally administering as a dietary supplement an amino acid formulation consisting of as the amino acid L-lysine or its physiologically acceptable salts in an amount sufficient to enhance the level of endothelial nitric oxide, whereby the development of said restenosis is inhibited.

5. A method of inhibiting the development of restenosis at an injury site in the vascular system of a human host, said method comprising:

administering an amino acid formulation consisting of as the amino acid L-lysine and its physiologically acceptable salts, in an amount sufficient to to provide a plasma level of said amino acid of 0.2 to 30 mM to enhance the level of endothelial nitric oxide at said injury site, whereby the development of said restenosis is inhibited.

6. A method according to claim 1, wherein said formulation is a health bar and said amino acids and their physiologically acceptable salts are in an amount of 2–25 g per bar.

7. A method according to claim 4, wherein said formulation is a health bar and said amino acid and its physiologically acceptable salts are in an amount of 2–25 g per bar.

8. A method according to any of claims 1 to 4 and 5 to 7, wherein said formulation comprises at least one of calcium, calmodulin, tetrahydrobiopterin, NADPH, or an amino acid absorption enhancing compound in sufficient amount to enhance the effect of said endothelial nitric oxide.

9. A method of inhibiting the development of atherosclerosis or restenosis in the vascular system of a human host susceptible to said atherosclerosis or restenosis, said method comprising:

orally administering as a dietary supplement an amino acid formulation consisting of the amino acid L-arginine hydrochloride and its physiologically acceptable salts, in an amount sufficient to enhance the level of endothelial nitric oxide whereby cholesterol level is unaffected by said endothelial nitric oxide and the development of said atherosclerosis or restenosis is inhibited.

10. A method according to claim 9, wherein said amount is at a daily dosage in the range of 3 to 12 g per day.

* * * * *

UNITED STATES PATENT AND TRADEMARK OFFICE
CERTIFICATE OF CORRECTION

PATENT NO. : 5,945,452
DATED : August 31, 1999
INVENTOR(S): J. P. Cooke, V. J. Dzau and G. H. Gibbons
TITLE : TREATMENT OF VASCULAR DEGENERATIVE DISEASES BY MODULATION OF ENDOGENOUS NITRIC OXIDE PRODUCTION OR ACTIVITY

It is certified that error appears in the above-identified patent and that said Letters Patent is hereby corrected as shown below:

In column 5, line 42, "su peroxide" should read --superoxide--.

In column 6, line 16, "No" should read --NO--.

In column 7, line 19, "su peroxide" should read --superoxide--.

In column 7, line 20, "su peroxide" should read --superoxide--.

In column 12, line 6, "No" should read --NO--.

Signed and Sealed this

Twenty-ninth Day of February, 2000

Attest:

Q. TODD DICKINSON

Attesting Officer

Commissioner of Patents and Trademarks

UNITED STATES PATENT AND TRADEMARK OFFICE
SECOND CERTIFICATE OF CORRECTION

PATENT NO. : 5,945,452
DATED : August 31, 1999
INVENTOR(S): J. P. Cooke, V. J. Dzau and G. H. Gibbons
TITLE : TREATMENT OF VASCULAR DEGENERATIVE DISEASES BY MODULATION OF ENDOGENOUS NITRIC OXIDE PRODUCTION OR ACTIVITY

It is certified that error appears in the above-identified patent and that said Letters Patent is hereby corrected as shown below:

In column 1, line 15, replace "Grant" with --Grants--;

Line 15, replace "(NHLBI)" with --and HL02668, both awarded by the National Institutes of Health--.

Signed and Sealed this

Eleventh Day of April, 2000

Attest:

Q. TODD DICKINSON

*Attesting Officer*          *Director of Patents and Trademarks*

UNITED STATES PATENT AND TRADEMARK OFFICE
Certificate

Patent No. 5,945,452                                                                                           Patented: August 31, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John P. Cooke, Palo Alto, CA (US).

Signed and Sealed this Sixteenth Day of January 2007.

WILLIAM R. DIXON, JR.
*Special Program Examiner*
Technology Center 1600